(12) United States Patent
Kast (10) Patent No.: US 9,119,671 B2
(45) Date of Patent: Sep. 1, 2015

(54) FIXATION ASSEMBLY FOR SPINAL VERTEBRAE

(75) Inventor: Erich Kast, Effretikon (CH)

(73) Assignee: ULRICH GMBH & CO. KG, Ulm (DE)

( * ) Notice: Subject to any disclaimer, the term of this patent is extended or adjusted under 35 U.S.C. 154(b) by 0 days.

(21) Appl. No.: 12/869,977

(22) Filed: Aug. 27, 2010

(65) Prior Publication Data

US 2011/0276094 A1 Nov. 10, 2011

(30) Foreign Application Priority Data

May 10, 2010 (DE) .......................... 10 2010 016 854

(51) Int. Cl.
*A61B 17/70* (2006.01)

(52) U.S. Cl.
CPC ......... *A61B 17/7025* (2013.01); *A61B 17/7026* (2013.01); *A61B 17/7046* (2013.01); *A61B 17/7014* (2013.01); *A61B 17/7032* (2013.01); *A61B 17/7035* (2013.01)

(58) Field of Classification Search
CPC .. A61B 17/864; A61B 17/70; A61B 17/7001; A61B 17/7004; A61B 17/7019; A61B 17/702; A61B 17/7026; A61B 17/7029; A61B 17/7031; A61B 17/7032–17/704

USPC .................................................. 606/246–279
See application file for complete search history.

(56) References Cited

U.S. PATENT DOCUMENTS

| | | | |
|---|---|---|---|
| 6,273,914 B1 | 8/2001 | Papas | |
| 7,029,475 B2 | 4/2006 | Panjabi | |
| 7,621,912 B2 | 11/2009 | Harms et al. | |
| 7,635,380 B2 | 12/2009 | Zucherman et al. | |
| 7,985,243 B2 | 7/2011 | Winslow et al. | |
| 2005/0085814 A1* | 4/2005 | Sherman et al. | 606/61 |
| 2005/0171543 A1* | 8/2005 | Timm et al. | 606/61 |
| 2008/0306525 A1* | 12/2008 | Mitchell et al. | 606/246 |
| 2010/0030267 A1* | 2/2010 | Winslow et al. | 606/246 |

FOREIGN PATENT DOCUMENTS

| | | |
|---|---|---|
| FR | 2694182 A1 | 7/1992 |
| WO | 2009/071813 A1 | 6/2009 |

* cited by examiner

*Primary Examiner* — Jerry Cumberledge
*Assistant Examiner* — Nicholas Plionis
(74) *Attorney, Agent, or Firm* — Andrew Wilford (57) ABSTRACT

A fixation assembly for spinal vertebrae has an anchor fixedly seatable in a spinal vertebrae and formed with an outwardly open socket, and a pedicle rod having a front end fixedly seated in the socket and a dynamic portion adjacent the front end that is shiftable relative to the anchor.

12 Claims, 10 Drawing Sheets

FIXATION ASSEMBLY FOR SPINAL VERTEBRAE

FIELD OF THE INVENTION

The present invention relates to a fixation assembly for spinal vertebrae.

BACKGROUND OF THE INVENTION

A typical fixation assembly for spinal vertebrae comprises an implant that is set into the vertebra body and a pedicle rod. In the standard such assembly the pedicle rod is solidly anchored in the implant and a connecting rod between two pedicle rods whose alignment can be varied. This configuration has the disadvantage that vertebrae are fixed relative to each other, that is there is virtually no possibility of relative movement.

Objects of the Invention

It is therefore an object of the present invention to provide an improved fixation assembly for spinal vertebrae.

Another object is the provision of such an improved fixation assembly for spinal vertebrae that overcomes the above-given disadvantages, in particular with respect to the range of motion.

SUMMARY OF THE INVENTION

A fixation assembly for spinal vertebrae. The assembly has according to the invention an anchor fixedly seatable in a spinal vertebrae and formed with an outwardly open socket, and a pedicle rod having a front end fixedly seated in the socket, and a dynamic portion adjacent the front end that is shiftable relative to the anchor.

Thus according to the invention the implant or anchor has a cavity or seat in which the pedicle rod can move relative to the implant. This configuration has the advantage that a dynamic segmental stabilization with a center of rotation in the region of the physiological center of rotation on the ventral side of the pedicle plane can be achieved. This way a substantially physiological movement pattern is obtained. An additional advantage is that an effective protection against adjacent segment degeneration as well as the conservation of a wider range of motion can be achieved.

It has proved to be advantageous if the implant is sleeve-shaped so that insertion of the implant into the vertebra is facilitated. Preferably, the pedicle rod has an elastic portion. Particularly preferred, the elastic section is made from a material selected from a group, comprising: metals and, in particular, titanium and its alloys, steel or CoCr, or plastic and, in particular, polyethylene, polyurethane, polyetherketone, carbon-fiber-reinforced plastic, or super-elastic nitinol. This configuration has the advantage that the mobility of the pedicle rod with respect to the implant can be achieved in a simple manner.

Furthermore, the fixation assembly can include an elastic element provided at a connecting region between the implant and the pedicle rod. This embodiment has the advantage that by using a damping element, additional stabilization can be achieved. For this purpose, for example, a hollow cylinder made of polycarbonate urethane (PCU) can be placed in the cavity between the inner surface of the cavity of the implant and the outer surface of the pedicle rod, the shape and geometry being varied to specifically established the desired damping and stabilization.

In a preferred embodiment, the implant is internally threaded the pedicle rod has an externally threaded inner end so that a solid but detachable connection between the implant and pedicle rod can be achieved. Moreover, other joining technologies such as, e.g. bonding, clamping, welding, snap-mounting or latching are also possible.

Moreover, a uniaxial, biaxial or polyaxial joint can be provided between the implant and the pedicle rod, the mobility, in particular flexion and extension, of the pedicle rod with respect to the implant being achieved in a simple manner. Thus there is in effect a pivoting at an elastically deformable region of the rod.

For the fixation assembly for vertebrae it has proved to be advantageous if the implant has an abutment face offset rearward from its front end and the pedicle rod has an abutment counterface for limiting mobility between the implant and the pedicle rod. The two faces are engageable radially as the pedicle rod flexes elastically.

Preferably, at its rear end the pedicle rod has a second closable connector-rod seat. In this connection it has proved to be particularly advantageous if the rod seat has an adjustable latch element. This configuration has the advantage that the generation of a fixed-angle connection can be done afterward with percutaneous intervention and, e.g. in case of critical bone conditions, an ingrowth of the implants is possible without load. After the ingrowth has taken place, the dorsal connection can be percutaneously closed under local anesthesia, whereby the dynamic or rigid segmental stabilization is activated.

For a fixation assembly for vertebrae according to the present invention it is advantageous if the pedicle rod has an oval cross section. By means of the oval cross-section, the range of motion for flexion and/or extension can be increased while maintaining the stability. Due to the oval cross-section, the moment of resistance can be different in different planes so that for example flexion is easier to perform than lateral bending. Furthermore, hereby, the stability during rotations is increased.

It is particularly advantageous, if the implant is formed as a sleeve with a rearwardly decreasing wall thickness.

Preferably, in the fixation assembly on one rear side, the implant has an extension configured with a coupling, in particular with a connector seat, for permanent attachment of a connector connected to a second fixation assembly. This configuration is particularly suitable for multi-segmental dynamic applications. To achieve a full dynamic range of motion, in particular regarding flexion/extension, over a plurality of segments it is necessary to compensate for length changes which occur in the region of the dorsal connectors so that the spacings and movements of the individual segments can be corrected. The connection between the individual dynamic fixation assemblies takes place in such a manner that in each case the pedicle rod of each fixation assembly is connected by a respective coupling means at the extension section with the nearest spinal implant sleeve. This way, stabilization of any desired length can be achieved. According to the present invention, this advantage can be achieved for a dorsal fixation system with a number of such fixation assemblies in that at least one fixation assembly has a connector connected by a mounting part of the first fixation assembly with the pedicle rod of the first fixation assembly and by the coupling means of the second fixation assembly with second fixation assembly.

According to a second aspect of the present invention, this object is solved for a dorsal fixation system in that a first fixation assembly for vertebrae according to any one of the above mentioned embodiments and a second fixation assembly for vertebrae with a connector are provided, the connector having a first mounting part with the first pedicle rod of the first fixation assembly and a second mounting part with the second pedicle rod of the second fixation assembly. This configuration has the advantage that by the more physiologically positioned center of rotation in the dorsal portion of the vertebra, a better segment mobility can be achieved. Thus the system can also be used for example as an intervertebral disk prosthesis. Furthermore, in a later stage, a combination with a facet joint replacement is also possible.

Preferably, in the dorsal fixation system, the first and/or the second mounting part are configured to set a first angle between the connector and the first pedicle rod of the first fixation assembly stable or, respectively, to set a second angle between the connector and the second pedicle rod of the second fixation assembly stable.

Alternatively, in the dorsal fixation system, the first mounting part and/or the second mounting part can be configured to establish a first angle between the connector and the first pedicle rod of the first fixation assembly variable or, respectively, to establish a second angle between the connector and the second pedicle rod of the second fixation assembly variable.

For the dorsal fixation system it is advantageous if the connector has a telescopic section and/or a flexible section to compensate for length changes occurring in the region of the dorsal connectors.

Preferably, the dorsal fixation system has a third fixation assembly for vertebrae and the connector is connected by a third mounting part at the third fixation assembly to a third pedicle rod of the third fixation assembly. In this manner, a multi-segmental dynamic stabilization can be achieved.

Another advantage of the fixation system according to the invention is that by the dorsal connector, segmental distraction is possible for example to continuously relieve the intervertebral disk.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
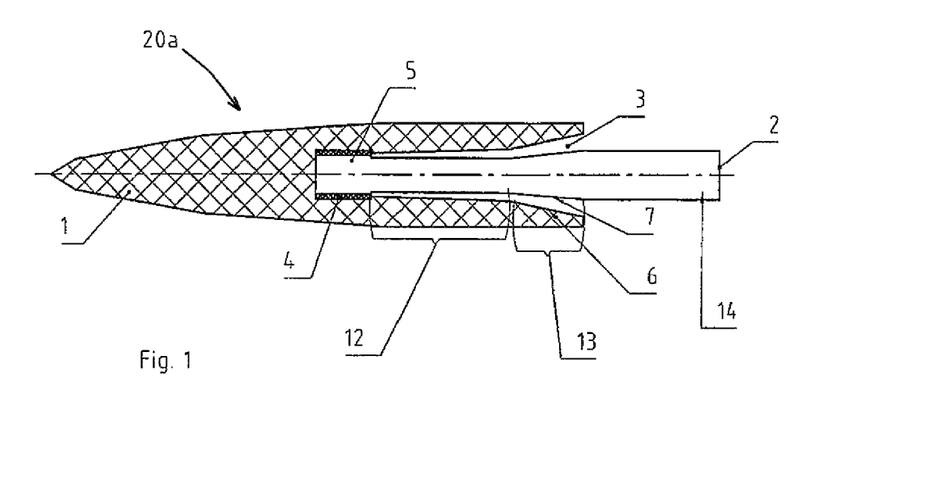
FIGS. 1, 2, 3, and 4 are sections through four embodiments of the present invention.

As seen in FIG. 1 a fixation assembly 20a for spinal vertebrae according to a first embodiment of the present invention comprises a socket implant or anchor 1 with a seat or cavity 3 and a pedicle rod 2. The implant cavity 3 has a threaded inner end 4 into which a threaded front end 5 of the pedicle rod 2 can be inserted, a diameter of 4 mm to 5 mm for the threaded front end 5 of the pedicle rod 2 having proven to be advantageous. Further, the implant 1 can have a frustoconically tapered shape with an external thread whose front (left hand in FIG. 1) portion can be blunt to allow bicortical anchoring. A rear portion of the external thread can become increasingly flatter and sharper to prevent the pedicle from breaking. Preferably, the surface of the implant is coated. The wall thickness of the implant 1 can be of decreasing thickness to the rear. The implant 1 can be inserted and anchored via a posterior transpedicular approach into the lumbar vertebrae, a sleeve-shaped configuration of the implant 1 having proven to be advantageous. Anchoring in the vertebra can be effected by the surface structure (such as for example the screwthread or coating) and/or deformation of the implant 1 (such as for example spreading, compressing, or ballooning).

The pedicle rod has a dynamic region 12, an anchoring region 14, and a motion-limiting region 13 in which contact of an abutment counterface 7 of the pedicle rod 2 on a frustoconical abutment face 6 of the implant 1 limits elastic deformation at 12 of the rod 2. Thus, the implant 1 and the pedicle rod 2 are formed in the rear region in such a manner that there is motion limited to a desired range. The permissible range of motion is determined in according to the configuration of the abutment face 6 of the implant 1 and the abutment counterface 7 of the pedicle rod 2.

To be able to better adapt the range of the dynamic deformation and the center of rotation to patient-specific requirements, the pedicle rod 2 can have different diameters and/or different configurations in the dynamic region 12 that deforms elastically. In the fixation assembly 20a according to the first embodiment shown in FIG. 1, the dynamic region 12 of the pedicle rod 2 has substantially the same diameter as the threaded front end 5, and the dynamic region 12 of the pedicle rod 2 is immediately adjacent the threaded front end 5. The inner surface of the seat 3 flares frustoconically outward to allow flexion of the region 12.

In the description of the further embodiments of the following figures, identical elements are denoted by identical reference numbers and that for avoiding repetitions, only the differences between the following embodiments are addressed.

Figure 2:
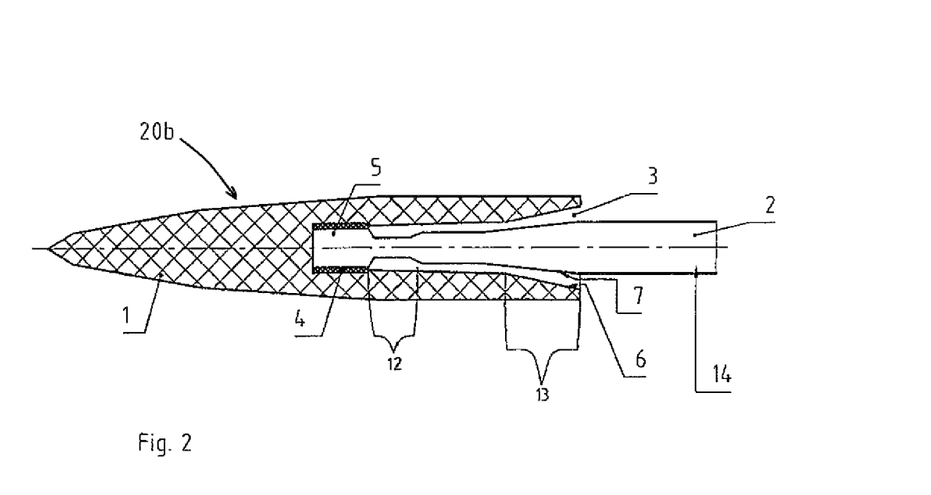

FIG. 2 shows a fixation assembly 20b for spinal vertebrae according to a second embodiment of the present invention in which the elastically deformable dynamic region 12 of the pedicle rod 2 has a smaller diameter than the threaded front end 5, and the dynamic region 12 of the pedicle rod 2 is immediately adjacent the threaded front end 5 of the pedicle rod 2.

Figure 3:
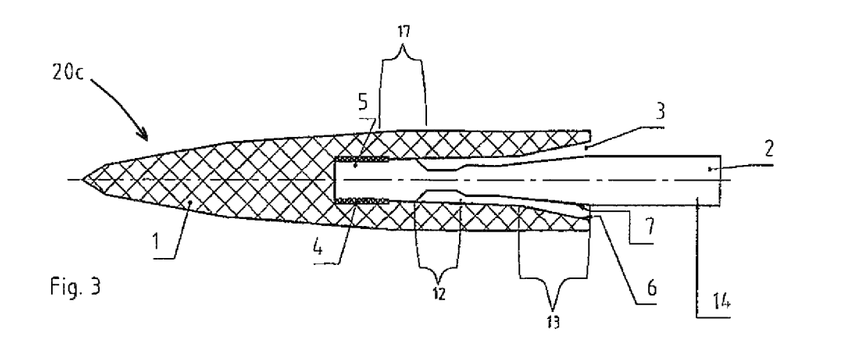

FIG. 3 shows a fixation assembly 20c for spinal vertebrae according to a third embodiment of the present invention where the dynamic region 12 of the pedicle rod 2 has a smaller diameter than the threaded front end 5, and between the dynamic region 12 of the pedicle rod 2 and the threaded front end 5 of the pedicle rod 2 there is a reinforcement region 17 with increased diameter.

Figure 4:
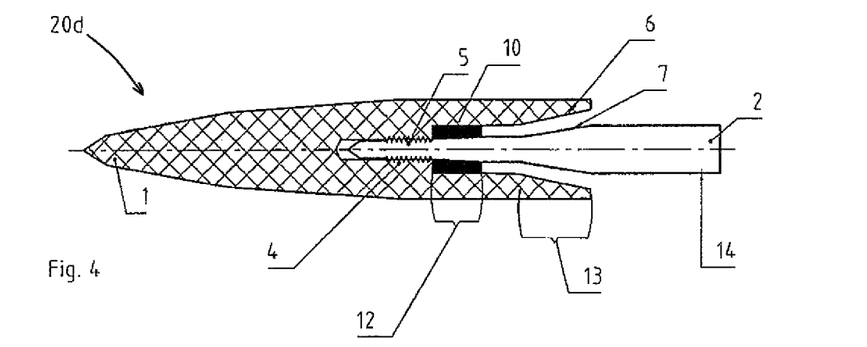

FIG. 4 shows a fixation assembly 20d for spinal vertebrae according to a fourth embodiment of the present invention, where the small-diameter dynamic region 12 of the pedicle rod 2 is immediately adjacent the threaded front end 5 of the pedicle rod 2, and where in addition, an elastic element 10 is arranged between the cylindrical outer surface of the dynamic region 12 of the pedicle rod 2 and the confronting cylindrical inner surface of the seat 3 of the implant 1. Thus, while the region 12 remains elastically deformable, its deformation is adjusted by the resilience of the elastic sleeve 10 filling the space between it and the inner face of the cavity 3.

Different configurations of the dynamic region can provide an optimal adaption to the specific needs of the respective patients. Furthermore, a rigid pedicle rod can be included in the system to allow a secondary change from a dynamic to rigid stabilization, or to allow a secondary change from a rigid to dynamic stabilization.

Figure 5:
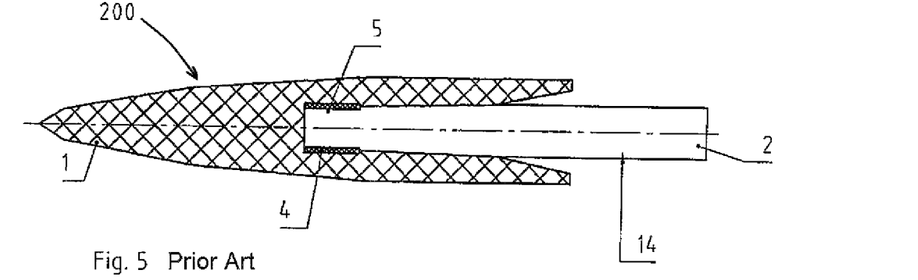
FIG. 5 is a view like FIGS. 1-4 of a prior-art assembly.

For a better understanding of the present invention, FIG. 5 shows a prior-art fixation assembly 200 for spinal vertebrae that comprises an implant and a pedicle rod 2 with neither a dynamic region nor a motion-limiting region so that only a rigid anchoring can take place.

Figure 6:
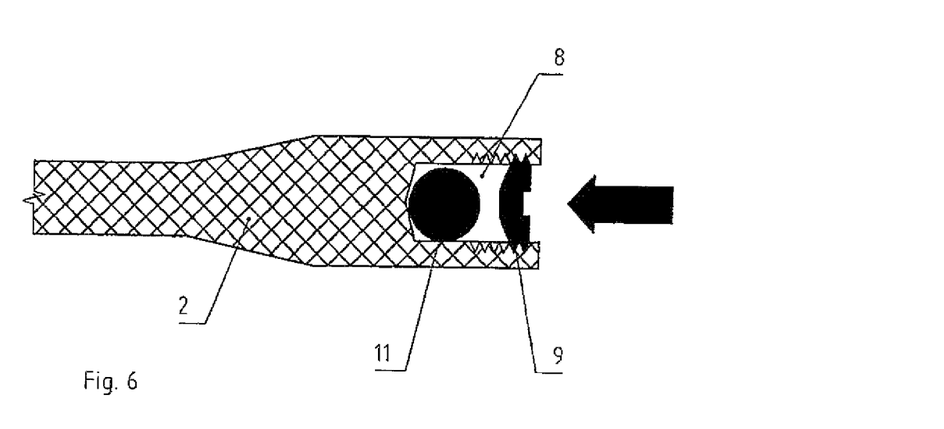
FIG. 6 is a section through a rear end of a pedicle rod with a connector.

FIG. 6 is a section through a pedicle rod 2 with a rear-end connector 11 for connection with another pedicle rod, the connector 11 preferably being formed as a cylindrical rod of uniform diameter. The rear end of the pedicle rod 2 has a closable rod seat 8 for the connector 11. To make the connection, a latch element 9 can be provided that, to make the connection effective, can be screwed in the direction of the arrow shown in FIG. 6 into the seat 8, thereby relatively fixing the connector 11 with the rod 2.

Figure 7:
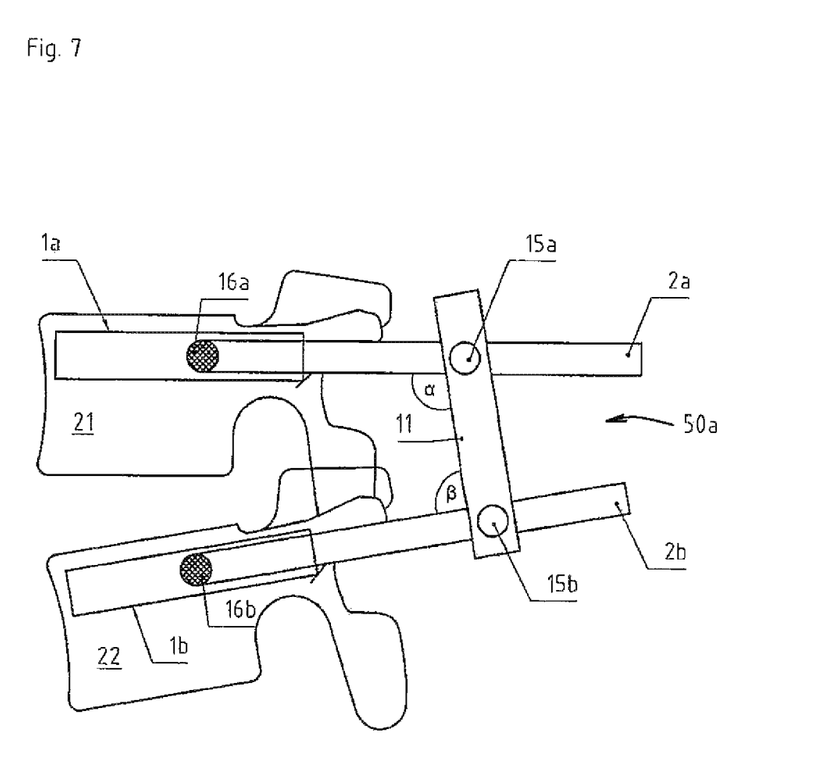
FIG. 7 is a vertical section through a fixation system having a pair of fixation assemblies according to the invention.

FIG. 7 shows a section through a dorsal fixation system 50 with a first fixation assembly 21 for spinal vertebrae according to the present invention and a second fixation assembly 22 for spinal vertebrae according to the present invention with a connector 11 that has a first mounting part 15a secured to a first pedicle rod 2a of the first fixation assembly 21 and a second mounting part 15b secured to a second pedicle rod 2b of the second fixation assembly 22, the rods 2a and 2b being seated in respective implants or anchors 1a. Alternatively, in the dorsal fixation assembly according to the present invention it is also possible that the first fixation assembly 21 or the second fixation assembly 22 be replaced by a conventional fixation assembly for spinal vertebrae with a rigid pedicle rod, which conventional fixation assembly is not shown in FIG. 7. In this manner, a combination of rigid and dynamic stabilization can be achieved.

Furthermore, in the embodiment shown in FIG. 7, the dorsal fixation system 50 has a first pivot axis 16a in the first fixation assembly 21 and a second pivot axis 16b in the second fixation assembly 22. The first mounting part 15a and/or the second mounting part 15b can be configured to maintain a first angle α between the connector 11 and the first pedicle rod 2a of the first fixation assembly 21 stable or a second angle β between the connector 11 and the second pedicle rod 2b of the second fixation assembly 22 stable. Alternatively, the first mounting part 15a and/or the second mounting part 15b can be configured to let the first angle α between the connector 11 and the first pedicle rod 2a of the first fixation assembly 21 be variable or to let the second angle β between the connector 11 and the second pedicle rod 2b of the second fixation assembly 22 vary.

Figure 8:
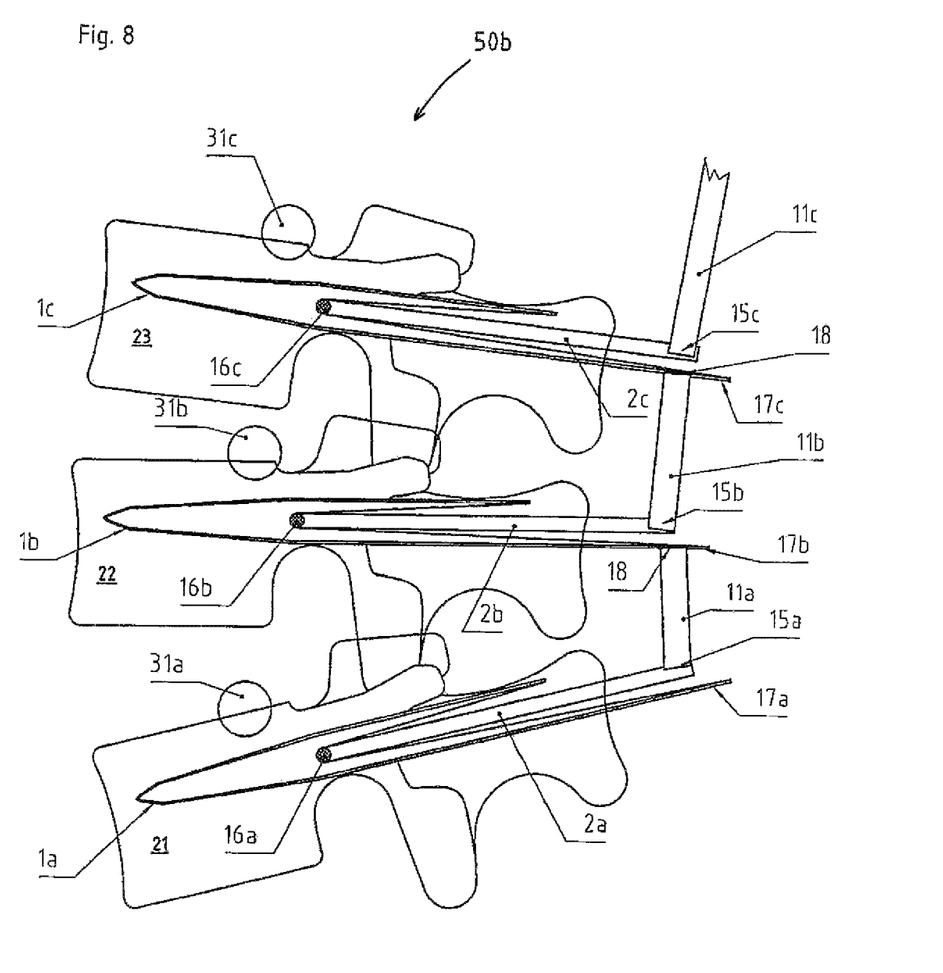
FIG. 8 is a vertical section through a second embodiment of the fixation system with three of the assemblies according to the invention.

Furthermore, in the dorsal fixation system according to the present invention, the number of fixation assemblies for spinal vertebrae is not limited to two, but it is also possible to use more fixation assemblies. FIG. 8 is a section through a dorsal fixation system 50b for multi-segmental applications according to a second embodiment with three fixation assemblies 21, 22, 23. Each of the fixation assemblies 21, 22, 23 has a respective pedicle rod 2a, 2b, 2c to each of which a respective connector 11a, 11b, 11c is attached by a respective mounting part 15a, 15b, 15c. Furthermore, the first and the second connectors 11a and 11b engage extensions 17b and 17c of the second and third implants 1b and 1c at 18, leaving an extension 17a of the first implant 1a free. In this embodiment, the physiological pivot axes 31a, 31b, 31c are at the mechanical pivot axes 16a, 16b, 16c.

Figure 9:
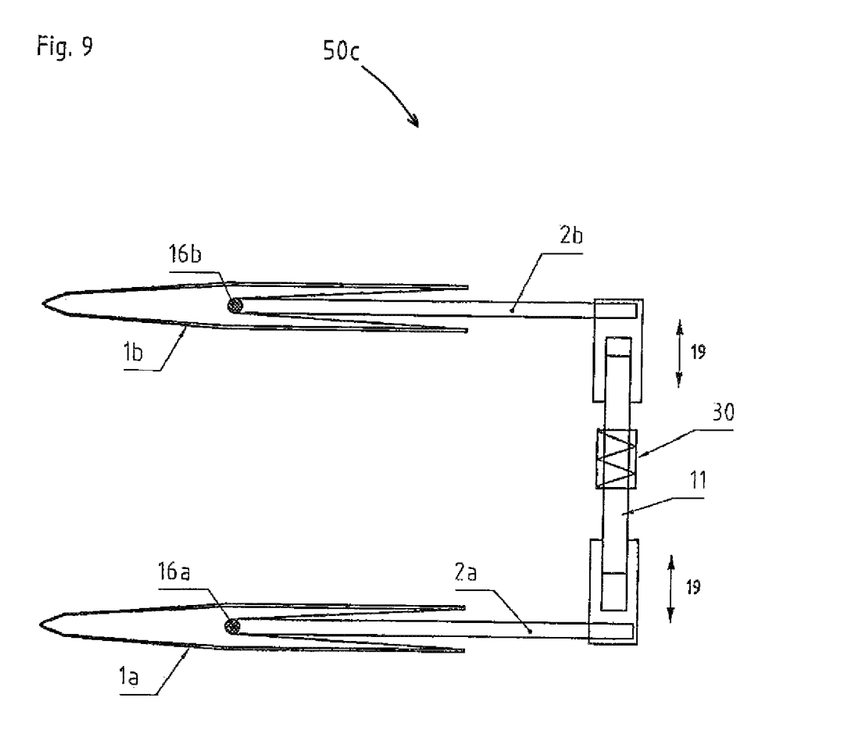
FIG. 9 is a vertical section through a third fixation system with two fixation assemblies and a flexible connector between them.

FIG. 9 is a section through a dorsal fixation system 50c with a flexible connector according to a third embodiment. The structure is similar to the embodiment shown in FIG. 7, but the connector 11 has a telescopic section 19 and a flexible section 30 which, in this case, is formed by a taper in the connector 11.

Figure 10:
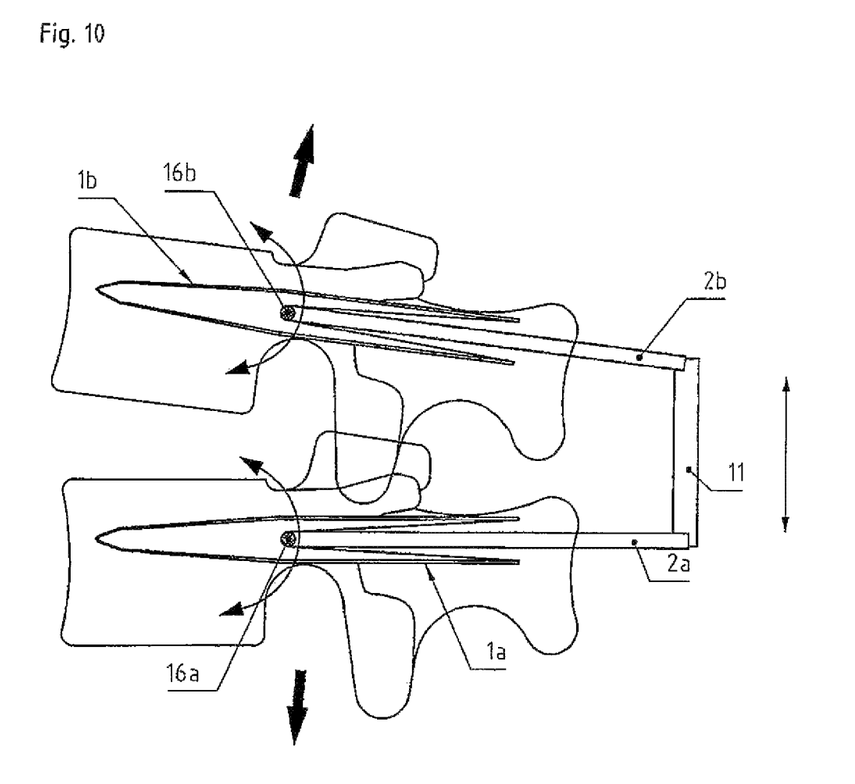
FIG. 10 is a view like FIG. 9 showing possibilities of movement with the system installed.
Figure 10A:
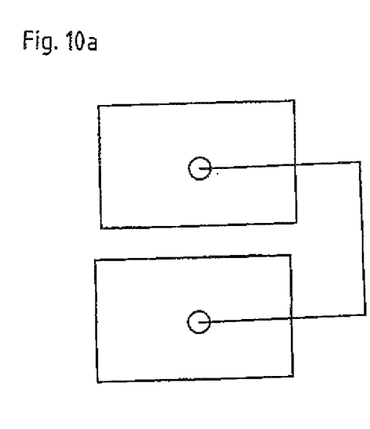
FIGS. 10a and 10b are schematic diagrams illustrating the invention.
Figure 10B:
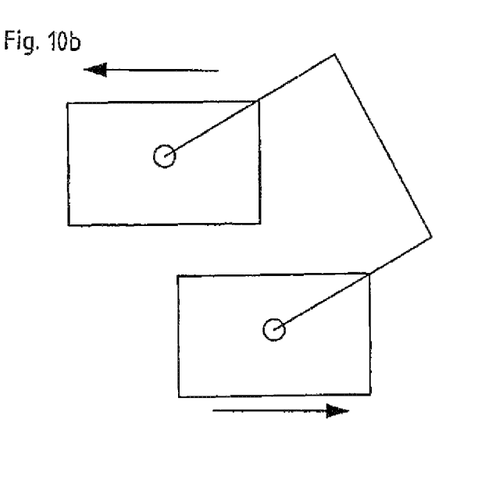

In FIGS. 10, 10a, and 10b are schematic illustrations of the movement possibilities of the dorsal fixation system with mono-segmental instrumentation. In addition to the rotation indicated by the arrows, a translation or straight-line movement is also possible. Moreover, by separation from the implant and the pedicle rod, possible screw loosening can be reduced since the dynamic movements are not transmitted via a bone-implant interface but via the implant-pedicle interface. Furthermore, a distraction takes place from the dorsal side by the pedicle rods and the longitudinal carrier so that the dynamic (range of motion) is maintained. Moreover, kyphosis can be avoided so that the saggital profile can be actively influenced without affecting the range of motion.

Figure 11:
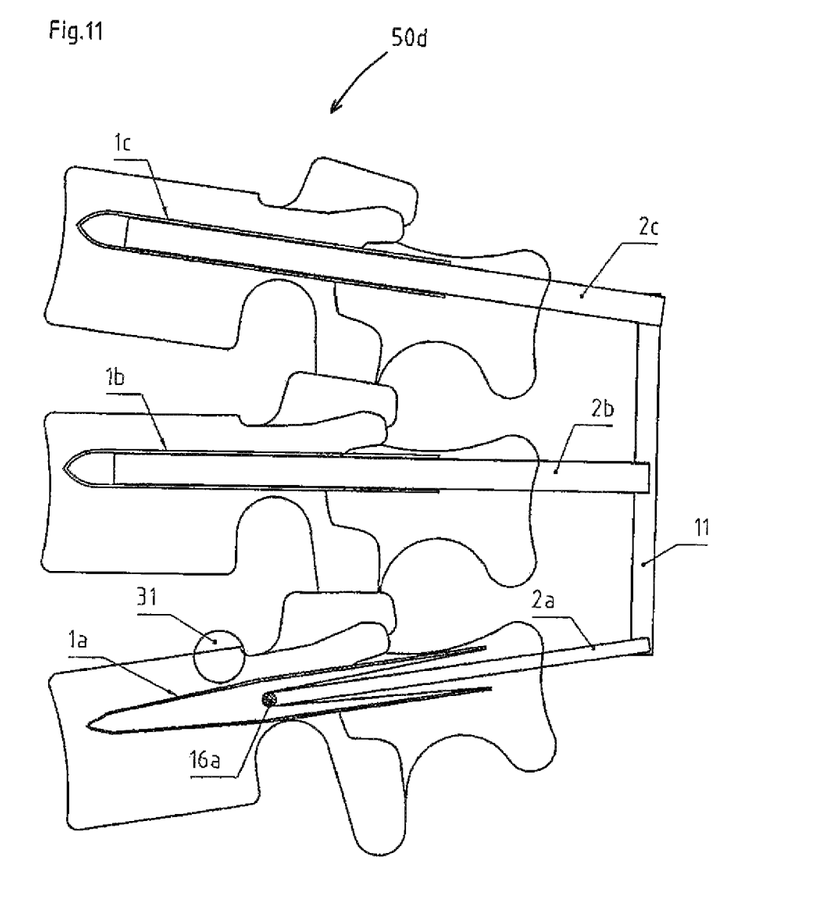
FIGS. 11, 12, and 13 are views like FIG. 10 of fourth, fifth, and sixth embodiments of the system with a third fixation.

FIG. 11 is a section through a dorsal fixation system 50d according to a fourth embodiment in which a physiological center of rotation 31 is located caudally in the vicinity of the mechanical center of rotation 16 of the implant. Thus, a rigid connector 11 is possible and for the second and third fixation assembly, conventional fixation assemblies can be used since no additional mobility is necessary. Thus, the dorsal fixation system 50d according to the fourth embodiment comprises one fixation assembly according to the invention and two conventional fixation assemblies.

Figure 12:
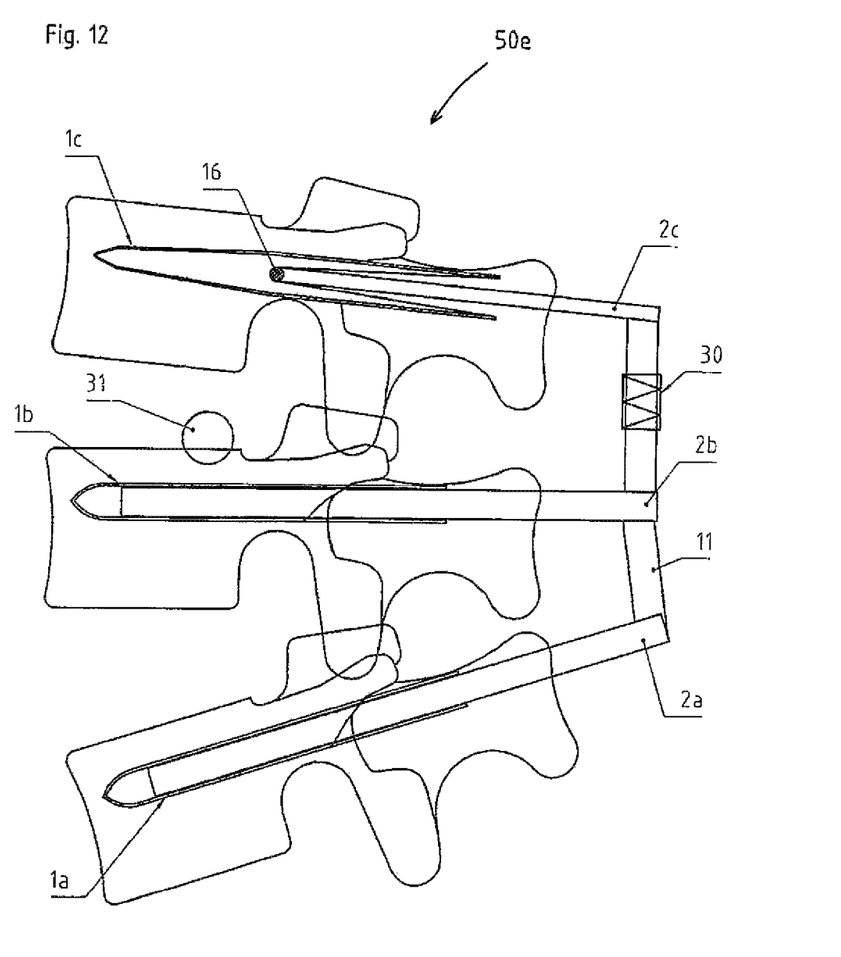

FIG. 12 is a section through a dorsal fixation system 50e according to a fifth embodiment in which the physiological center of rotation 31 is remote from the mechanical center of rotation 16 so that a second movement is necessary. This requires a dynamic connector 11. As shown FIG. 12, this can be achieved by a flexible section 30 formed for example by a taper. Again, the dorsal fixation system 50e according to the fifth embodiment comprises one fixation assembly according to the invention and two conventional fixation assemblies.

Figure 13:
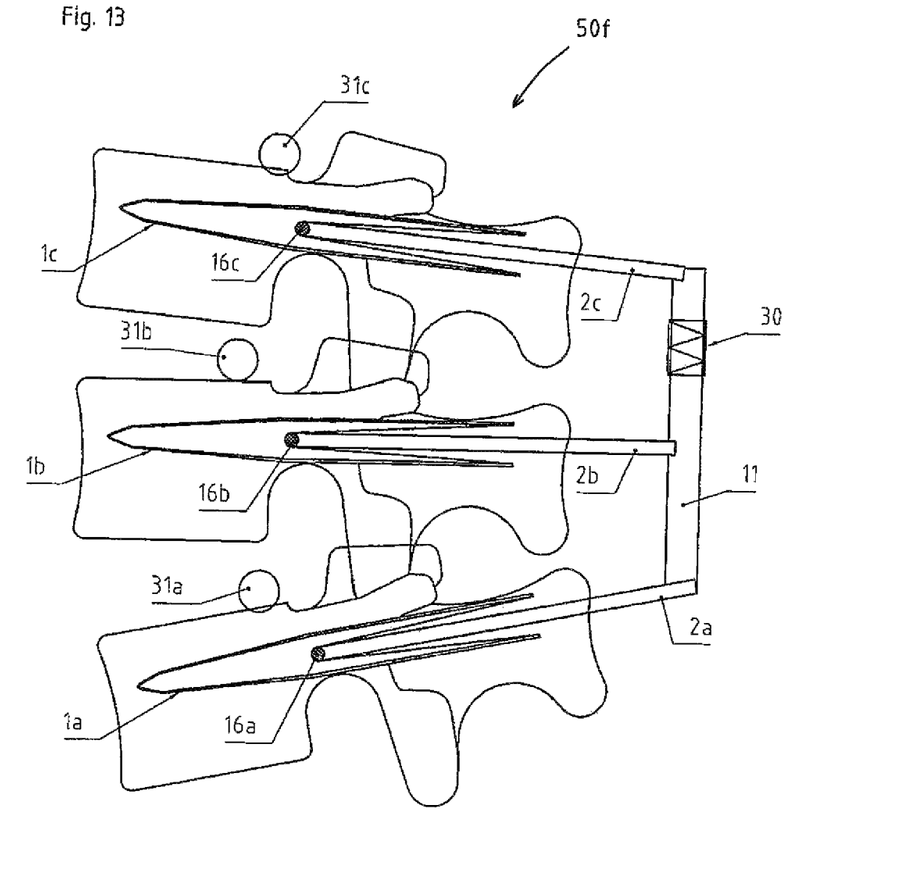

FIG. 13 is a section through a dorsal fixation system 50f according to a sixth embodiment with three fixation assemblies according to the invention, the three physiological centers of rotation 31a, 31b, 31c being located caudally in the vicinity of the three mechanical centers of rotation 16a, 16b, 16c. In contrast to a mono-segmental instrumentation in which two ranges of motion are sufficient to achieve flexion and translation, in the present multi-segmental instrumentation, further ranges of motion are necessary which are formed as taper in the embodiment present in FIG. 13.

I claim:

1. A fixation assembly for spinal vertebrae, the assembly comprising:
 a first anchor sleeve fixedly seatable in a spinal vertebra, having a longitudinal axis, and formed with an outwardly axially extending and open socket having an axially inner end region formed with an internal screwthread and a sleeve-shaped axially outer end region formed with a radially inwardly directed abutment surface and on one side only with an axially rearward extension such that the outer end region of the first sleeve is asymmetrical;
 a first one-piece metallic pedicle rod extending along the axis and having an inner end formed with an external screwthread fixedly seated in the internal screwthread of the inner end region of the socket, an elastically deformable dynamic portion extending axially outward from the inner end, and an outer end extending axially outward from the dynamic portion past the other of the sides of the outer end region of the first sleeve and having therein an outer surface spaced radially from the abutment surface of the outer end region of the first sleeve, whereby elastic radial deflection of the outer end engages the outer surface of the outer end with the inwardly directed abutment surface of the first sleeve, the rearward extension projecting axially outward past the outer end of the first pedicle rod; and a connector bearing transversely of the axis on the rearward extension of the first anchor sleeve and fixed to an outer end of a second pedicle rod seated in a second anchor sleeve anchorable in an adjacent vertebra.

2. The fixation assembly defined in claim 1, wherein the dynamic portion is formed of titanium, a titanium alloy, steel, nickel-titanium alloy, memory metal, or CoCr.

3. The fixation assembly defined in claim 1, further comprising:

an elastic element between and engaging an inner wall of the socket of the first sleeve and the respective dynamic portion of the first pedicle rod axially outward of the screwthreads.

4. The fixation assembly defined in claim 1, wherein a rear end of the first pedicle rod is formed with a closable anchor seat.

5. The fixation assembly defined in claim 4, further comprising an element shiftable axially of the first pedicle rod for closing the anchor seat.

6. The fixation assembly defined in claim 1, wherein the pedicle rod has an oval cross section.

7. The fixation assembly defined in claim 1, wherein the rearward extension is of decreasing wall thickness axially away from the inner end of the first pedicle rod.

8. The fixation assembly defined in claim 1, wherein the second anchor sleeve has a respective rearward extension, the assembly further comprising:

a third anchor sleeve anchorable in another respective adjacent vertebra and having a respective third such rearward extension, a third pedicle rod seated in the third anchor sleeve, and another connector bearing on the rearward extension of the second anchor sleeve and fixed to an outer end of the third pedicle rod of the third anchor sleeve.

9. The fixation system defined in claim 1, wherein the first anchor sleeve has an outer surface constructed so as to fixedly bond or secure to the vertebra.

10. The fixation system defined in claim 1, wherein the first anchor sleeve is of one piece.

11. A fixation system for two adjacent spinal vertebrae, the system comprising:

first and second anchor sleeves fixedly seatable in respective adjacent vertebrae, each having a respective longitudinal axis, and each formed with an outwardly axially extending and open socket having an axially inner end region formed with an internal screwthread and a sleeve-shaped axially outer end region formed with a radially inwardly directed abutment surface and on one side only with an axially rearward extension such that the outer end region of the sleeve is asymmetrical;

respective first and second pedicle rods each having a front end formed with an external screwthread fixedly seated in the internal screwthread of the inner end of a respective one of the sockets of the first and second sleeves and spacedly received in the respective anchor sleeve, each pedicle rod having a dynamic portion adjacent the front end, in the respective socket, that is shiftable relative to the respective anchor sleeve, and a rear end;

a connector extending transversely of the axes between the rear end of the second pedicle rod and the rearward extension of the first anchor sleeve.

12. The fixation system defined in claim 11, wherein the second pedicle rod and rearward extension of the first sleeve form different angles with the connector and the second pedicle rod, rearward extension of the first sleeve, and connector are angularly relatively fixed.

* * * * *